United States Patent
Alvarez et al.

(10) Patent No.: US 8,614,096 B2
(45) Date of Patent: Dec. 24, 2013

(54) HUMIDITY AND TEMPERATURE CORRECTIONS TO IMPROVE ACCURACY OF HF AMBIENT AIR MONITORS BASED ON TUNABLE DIODE LASER IR ABSORPTION MEASUREMENTS

(75) Inventors: Manuel S. Alvarez, Warrenton, VA (US); David B. Spry, Vienna, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 2800 days.

(21) Appl. No.: 13/223,756

(22) Filed: Sep. 1, 2011

(65) Prior Publication Data

US 2013/0059395 A1   Mar. 7, 2013

(51) Int. Cl.
*G01N 33/00* (2006.01)

(52) U.S. Cl.
USPC ........... 436/101; 436/164; 436/181; 356/437; 250/339.12; 250/339.13; 250/339.06; 250/339.07; 250/338.1; 250/338.5

(58) Field of Classification Search
None
See application file for complete search history.

(56) References Cited

U.S. PATENT DOCUMENTS

| 4,535,241 | A | 8/1985 | Eberhardt |
| 5,075,550 | A | 12/1991 | Miller et al. |
| 2008/0179530 | A1 | 7/2008 | Liu et al. |

FOREIGN PATENT DOCUMENTS

| DE | 3116344 A1 | 11/1982 |
| WO | 9411713 A1 | 5/1994 |

OTHER PUBLICATIONS

Zvereva, N.A., et al. IR spectra of HF and its complex with water under real atmospheric conditions, 2001, Optika Atmosfery i Okeana, vol. 14(12), pp. 1099-1102.*

PCT International Search Report issued Nov. 15, 2012 in corresponding PCT Application No. PCT/US2012/053278, 4 pgs.
PCT Written Opinion issued Nov. 15, 2012 in corresponding PCT Application No. PCT/US2012/053278, 7 pgs.
K. Pfeilsticker, "Atmospheric Detection of Water Dimers via Near-Infrared Absorption", Science, vol. 300, No. 5628, Jun. 27, 2003, pp. 2078-2080.
S.L.A.Adebayo et al, Thermodynamic Properties of Hydrogen-bonded Dimers B . . . HF from Spectroscopy: B = HCN, CH3CN, HC2CN, (CH3)3CCN and H20, J. Chem Soc. Faraday Trans, 1991, 87(3), 443-447.
J.F. Gaw et al, "Vibrational Frequency Shifts in Hydrogen-Bonded Systems: The Hydrogen Fluoride Dimer and Trimer" J. Am. Chem. Soc. 1984 (106), 3133-3138.
A.S. Pine et al., Rotational Structure and Vibrational Predissociation in the HF Stretching Bands of the HF Dimer, J. Chem. Physics, Mar. 1, 1983, 78(5), 2154-2161.
Redington, "Nonideal-Associated Vapor Analysis of Hydrogen Fluoride", J. Phys. Chem, 1982, 86, 552-560.

* cited by examiner

*Primary Examiner* — Robert Xu
(74) *Attorney, Agent, or Firm* — Glenn T. Barrett (57) ABSTRACT

Method of determining a total HF concentration metric in an environment including measuring an uncorrected HF concentration metric in the environment based on a first infrared absorption measurement at a wavelength corresponding to a vibrational frequency of a non-hydrogen bonded gas phase HF molecule; determining an ambient $H_2O$ concentration metric in the environment available for reaction with the non-hydrogen bonded gas phase HF molecules at or about the time of obtaining the first infrared absorption measurement; calculating a HF hydrate concentration metric in the environment based on the uncorrected HF concentration metric, the ambient $H_2O$ concentration metric and a reaction equilibrium relationship between the non-hydrogen bonded gas phase HF molecule and the HF hydrate; and determining the total HF concentration metric in the environment based on the uncorrected HF concentration metric and an amount of HF determined by the HF hydrate concentration metric.

6 Claims, 4 Drawing Sheets

HUMIDITY AND TEMPERATURE CORRECTIONS TO IMPROVE ACCURACY OF HF AMBIENT AIR MONITORS BASED ON TUNABLE DIODE LASER IR ABSORPTION MEASUREMENTS

FIELD

The disclosed subject matter relates to methods and systems for improved hydrofluoric acid (HF) detection and quantification based on infrared light absorption. In particular, the disclosed subject matter relates to the determination of a total HF concentration metric based upon a measured, uncorrected HF concentration metric and an HF hydrate concentration metric.

BACKGROUND

Commercially available hydrofluoric acid detectors, which can be based on infrared (IR) light absorption using Tunable Diode Lasers (TDL), are used in alkylation units in petrochemical refineries to monitor background HF concentrations, detect accidental releases for Safety, Health and Environmental (SHE) applications and to initiate mitigation actions. These sensors target HF monomers as the light absorbing species. The TDL light source generates light that is absorbed by HF in a very narrow wavelength range, making the detectors very specific to HF.

HF has three pairs of localized sp3 electrons that do not participate in covalent bonding. These non-bonding electrons make HF a very strong hydrogen bonding molecule. This is typical of hydrides formed by the second row elements in the periodic table (e.g., $NH_3$, $H_2O$ and HF). The strong tendency to form hydrogen bonds leads to the formation of gaseous polymers of HF (e.g., $(HF)_2$, $(HF)_4$ and $(HF)_6$). In addition, this same characteristic leads to the formation of hydrates (i.e., water molecules hydrogen bonded to HF). The formation of polymers and hydrates broadens and distorts the HF absorption spectrum.

Nevertheless, commercially available TDL detectors target the monomer for detection. The abundance of the HF monomer in ambient air is dependent on the ambient temperature and humidity, since some of the monomers that would otherwise be present form hydrates at higher humidities. As a result, the actual HF concentration in the airspace can be underreported. Effects of underreporting are amplified in newer point detectors based on TDL technologies that allow for detection at low concentration levels of interest (HF TLV=3 ppmv), and reduced interference from other chemical compounds. Even in earlier open path TDL models, that provide an average concentration over the monitored line of sight path, the average measured value would still be underreported. Thus, the open path sensors could also benefit by the application of the same ambient humidity and temperature correction.

Thus, there remains a need for HF detectors that can accurately output the true amount of HF in an air space, including HF that is contributed in hydrate form.

SUMMARY

One aspect of the presently disclosed subject matter provides a method of determining a total HF concentration metric in an environment including measuring an uncorrected HF concentration metric in the environment based on a first infrared absorption measurement at a wavelength corresponding to a vibrational frequency of a non-hydrogen bonded gas phase HF molecule, determining an ambient $H_2O$ concentration metric in the environment available for reaction with the non-hydrogen bonded gas phase HF molecules at or about the time of obtaining the first infrared absorption measurement, calculating a HF hydrate concentration metric in the environment based on the uncorrected HF concentration metric, the ambient $H_2O$ concentration metric and a reaction equilibrium relationship between the non-hydrogen bonded gas phase HF molecule and the HF hydrate, and determining the total HF concentration metric in the environment based on the uncorrected HF concentration metric and an amount of HF determined by the HF hydrate concentration metric.

Another aspect of the presently disclosed subject matter provides a spectroscopy system for performing infrared spectroscopy to output a HF concentration metric including a detector capable of measuring infrared light absorption at a pre-selected frequency corresponding to the vibrational frequency of a non-hydrogen bonded gas phase HF molecule to output an uncorrected HF concentration metric, a hygrometer to measure ambient water concentration to output an ambient $H_2O$ concentration metric, and a processor in electronic communication with the detector and hygrometer, to receive outputs from the detector and hygrometer and to output the HF concentration metric.

DETAILED DESCRIPTION

Reference will now be made in detail to non-limiting embodiments of the disclosed subject matter. Technical descriptions and equations are provided for purposes of illustration and not limitation.

One aspect of the presently disclosed subject matter provides a method of determining a total HF concentration metric in an environment including measuring an uncorrected HF concentration metric in the environment based on a first infrared absorption measurement at a wavelength corresponding to a vibrational frequency of a non-hydrogen bonded gas phase HF molecule, determining an ambient $H_2O$ concentration metric in the environment available for reaction with the non-hydrogen bonded gas phase HF molecules at or about the time of obtaining the first infrared absorption measurement, calculating a HF hydrate concentration metric in the environment based on the uncorrected HF concentration metric, the ambient $H_2O$ concentration metric and a reaction equilibrium relationship between the non-hydrogen bonded gas phase HF molecule and the HF hydrate, and determining the total HF concentration metric in the environment based on the uncorrected HF concentration metric and an amount of HF determined by the HF hydrate concentration metric.

The infrared absorption measurement can be obtained via an apparatus that employs a tunable diode laser. The ambient $H_2O$ concentration metric can be determined based on the ambient temperature and a humidity metric selected from relative humidity and dew point, at or about the time of obtaining the first infrared absorption measurement.

Alternatively, the ambient $H_2O$ concentration metric can be determined by directly measuring the $H_2O$ concentration in the sample space. For example, the ambient $H_2O$ concentration metric can be determined by measuring a second infrared absorption measurement at a wavelength corresponding to $H_2O$ absorption (e.g., at a wavelength corresponding to a vibrational or rotational frequency of an H—O bond within $H_2O$ molecules) at or about the time of obtaining the first infrared absorption measurement. Thus, the rotational and/or vibrational spectrum of water can be used to directly ascertain the $H_2O$ concentration metric.

In one embodiment, the reaction equilibrium relationship between the gas phase HF molecules and the HF hydrate is based at least in part on the equilibrium constant, $K_{eq}(T)$, for the reaction $H_2O+HF \leftrightarrow HF\cdot H_2O$ at the ambient temperature. The equilibrium constant, $K_{eq}(T)$, for the reaction $H_2O+HF \leftrightarrow HF\cdot H_2O$ at the ambient temperature can be calculated based at least in part on thermodynamic parameters for the hydrogen bonding reaction associated with the HF hydrate at the ambient temperature.

Another aspect of the presently disclosed subject matter provides a method for calibrating an HF ambient air monitor including providing a carrier gas, introducing a constant, known flow of HF to the carrier gas to obtain a calibration sample, introducing the calibration sample to the HF ambient air monitor and measuring a first infrared absorption measurement at a wavelength corresponding to a vibrational frequency of an H—F bond within non-hydrogen bonded gas phase HF molecules, determining a carrier gas $H_2O$ concentration metric in the calibration sample available for reaction with non-hydrogen bonded gas phase HF molecules present in the calibration sample at or about the time of obtaining the first infrared absorption measurement, calculating an uncorrected HF concentration metric in the calibration sample based on the constant, known flow of HF to the carrier gas, the carrier gas $H_2O$ concentration metric and the reaction equilibrium relationship between non-hydrogen bonded gas phase HF molecules and HF hydrate, and calibrating the HF ambient air monitor based on the first infrared absorption measurement and the uncorrected HF concentration metric in the calibration sample.

In one embodiment, the carrier gas is air. The constant, known flow of HF can be introduced to the carrier gas by passing the carrier gas over a porous tube containing HF, in which the porous tube has a known HF diffusion rate. The ambient air monitor can be an apparatus that employs a tunable diode laser.

The carrier gas $H_2O$ concentration metric can be determined based on the temperature of the carrier gas and a humidity metric of the carrier gas selected from relative humidity and dew point, at or about the time of obtaining the first infrared absorption measurement. Alternatively, the carrier gas $H_2O$ concentration metric can be determined by measuring a second infrared absorption measurement at a wavelength corresponding to a vibrational frequency of an H—O bond within $H_2O$ molecules in the carrier gas at or about the time of obtaining the first infrared absorption measurement.

Yet another aspect of the presently disclosed subject matter provides a spectroscopy system for performing infrared spectroscopy to output a HF concentration metric including a detector capable of measuring infrared light absorption at a pre-selected frequency corresponding to the vibrational frequency of a non-hydrogen bonded gas phase HF molecule to output an uncorrected HF concentration metric, a hygrometer to measure ambient water concentration to output an ambient $H_2O$ concentration metric, and a processor in electronic communication with the detector and hygrometer, to receive outputs from the detector and hygrometer and to output the HF concentration metric. In one embodiment, the system can further include a thermocouple in electronic communication with the processor to measure ambient temperature. The spectroscopy system can be in the form of, for example, a tunable diode laser system, a Fourier transformed infrared system (FTIR) or a multipath cell system that employs other spectroscopic techniques.

The processor can be located within the detector itself. Alternatively, the detector can be a separate piece of equipment, located external to the detector (e.g., a stand alone computer, a distributed control system (DCS) or other programmable logic controller (PLC)).

As discussed above, a given measurement can be obtained or determined at or about the time of a second measurement. For example, the method can include determining an ambient $H_2O$ concentration metric in the environment available for reaction with the non-hydrogen bonded gas phase HF molecules at or about the time of obtaining the first infrared absorption measurement. As used herein, "at or about the time," as used above, can refer to simultaneous measurement and determination, or measurement or determination in such close proximity to each other such that the two measurements or determinations can functionally be considered to occur at the same time without substantively changing the results.

In one embodiment, "at or about the same time" can refer to a first measurement or determination within about 8 hours. Particularly, the measurement or determination can be within about 4 hours, within about 2 hours, within about 1 hour, or within about 15 minutes of the second measurement or determination.

Systems of the present application can include a hygrometer. As used herein, "a hygrometer" can refer to any device that provides or otherwise determines a water concentration metric. For example, systems of certain embodiments can employ detectors that directly measure water concentrations or metrics, such as by measuring the absorption spectrum that corresponds to water. Also, the systems can contain a processor in which, for example, a user-entered humidity and temperature is received and the water concentration is determined from the inputted data. As used herein, each of the above-described systems is considered to include a hygrometer.

Hydrofluoric acid, or HF, forms a strong hydrogen bond with water in the vapor phase to form a $H_2O$—HF complex.

$$H_2O + HF \underset{}{\overset{K_{eq}}{\rightleftharpoons}} H_2O \cdot HF \quad \text{(Eq. 1)}$$

Free HF           Complexed HF

Common HF area safety detectors use vibrational spectroscopy and measure infrared light absorption of the precise HF bond vibrational frequency. As HF hydrogen bonds with water, its vibrational frequency is shifted to a lower frequency and it is undetected by current safety devices that rely on infrared spectroscopy. Previous spectroscopic studies have observed the gas phase vibrational frequency of HF to decrease by 270 $cm^{-1}$ when hydrogen bonding to water. See J. F. Gaw, Y. Yamaguchi, M. A. Vincent, H. F. Schaefer III,

*JACS*, 106, 3133 (1984); K. P Huber and G. Herzberg, "*Constants of Diatomic Molecules*", Van Nostrand-Reinhold, New York (1979); and A. S. Pine and W. J. Lafferty, *J. Chem. Phys.*, 78, 2154 (1983), each of which are hereby incorporated by reference in their entirety.

The equilibrium of the hydrogen bonding reaction is disclosed in the literature. The enthalpy and entropy of the reaction are −39.1 kJ/mol and −94.4 J/mol·K at 25° C., respectively. See, S. L. A. Adebayo, A. C. Legon, and D. J. Millen, *J. Chem. Soc. Faraday Trans.*, 87, 443 (1991), which is hereby incorporated by reference.

The equilibrium constant favors the hydrogen bonded species at room temperature, with $K_{eq} \sim 100$. The ratio of bound to unbound HF species can be expressed as $$\frac{[H_2O - HF]}{[HF]} = K_{eq}(T)[H_2O]. \qquad (Eq.\ 2)$$

Figure 1:
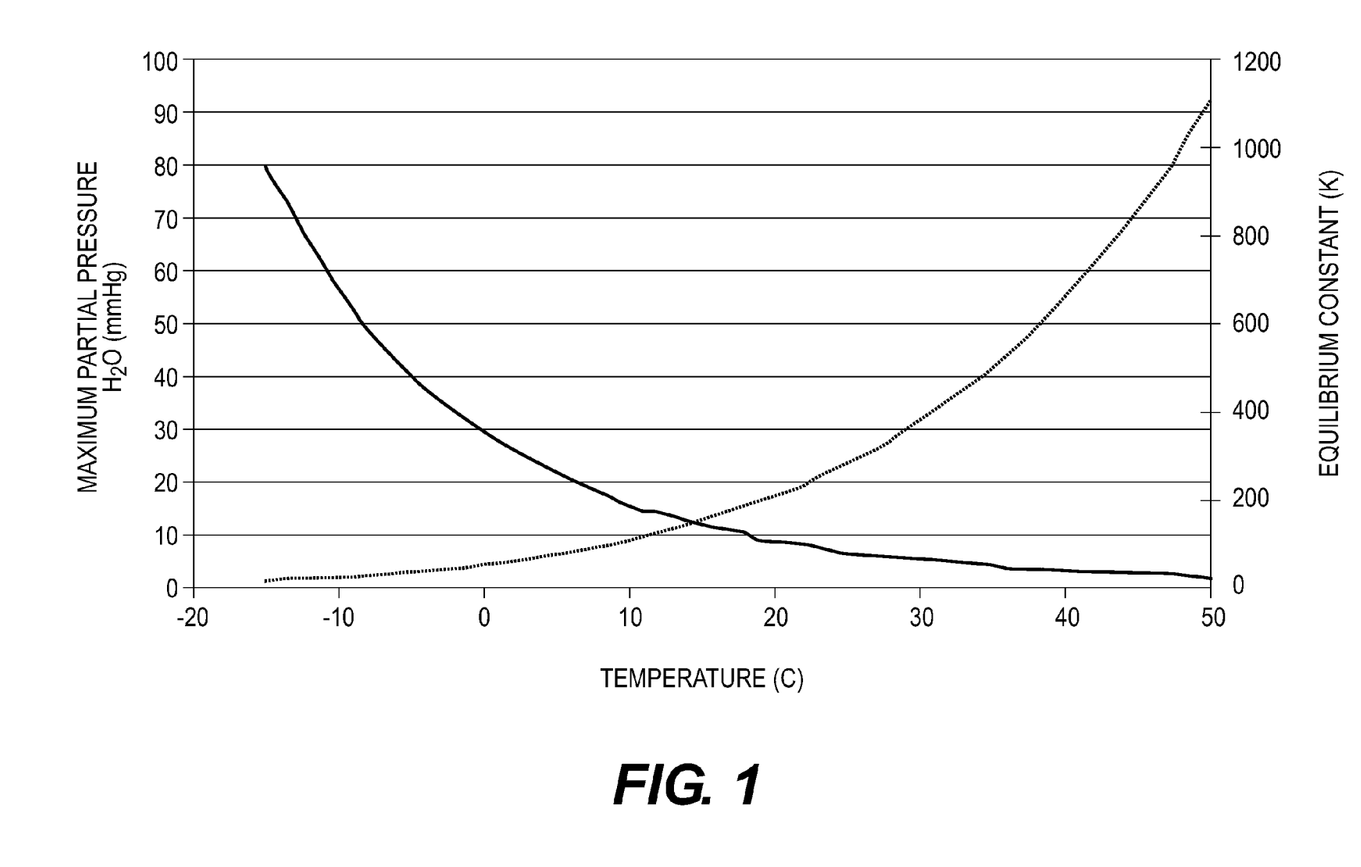
FIG. 1 is a plot of the equilibrium constant of the hydrogen bonding reaction and the maximum partial pressure of water in the atmosphere (100% relative humidity) as a function of temperature.

The equilibrium constant, $K_{eq}(T)$, is temperature dependant. Although the hydrogen bond is very strong, the entropy of the hydrogen bonding reaction is highly negative, which decreases the favorability of the reaction at high temperatures. As shown in FIG. 1 by the line plot having a decreasing slope, equilibrium constant of the hydrogen bonding reaction decreases as temperature increases.

At relatively low atmospheric humidity levels, which results in a small $[H_2O]$, the majority of the population exists in the unbound state and the current methods of detection that rely on vibrational spectroscopy of the unbound HF species yield more accurate results. The maximum amount of water that can be carried in the atmosphere, referred to as 100% humidity, is highly dependent upon temperature. The saturation vapor pressure of water increases dramatically with increasing temperature. This is shown in FIG. 1 by the plot having the increasing scope, which depicts the maximum partial pressure of water in the atmosphere (100% relative humidity) as a function of temperature. At higher temperatures there is much more water in the atmosphere available for hydrogen bonding with the HF, which drives the hydrogen bonding reaction to favor the complexed species.

Figure 2:
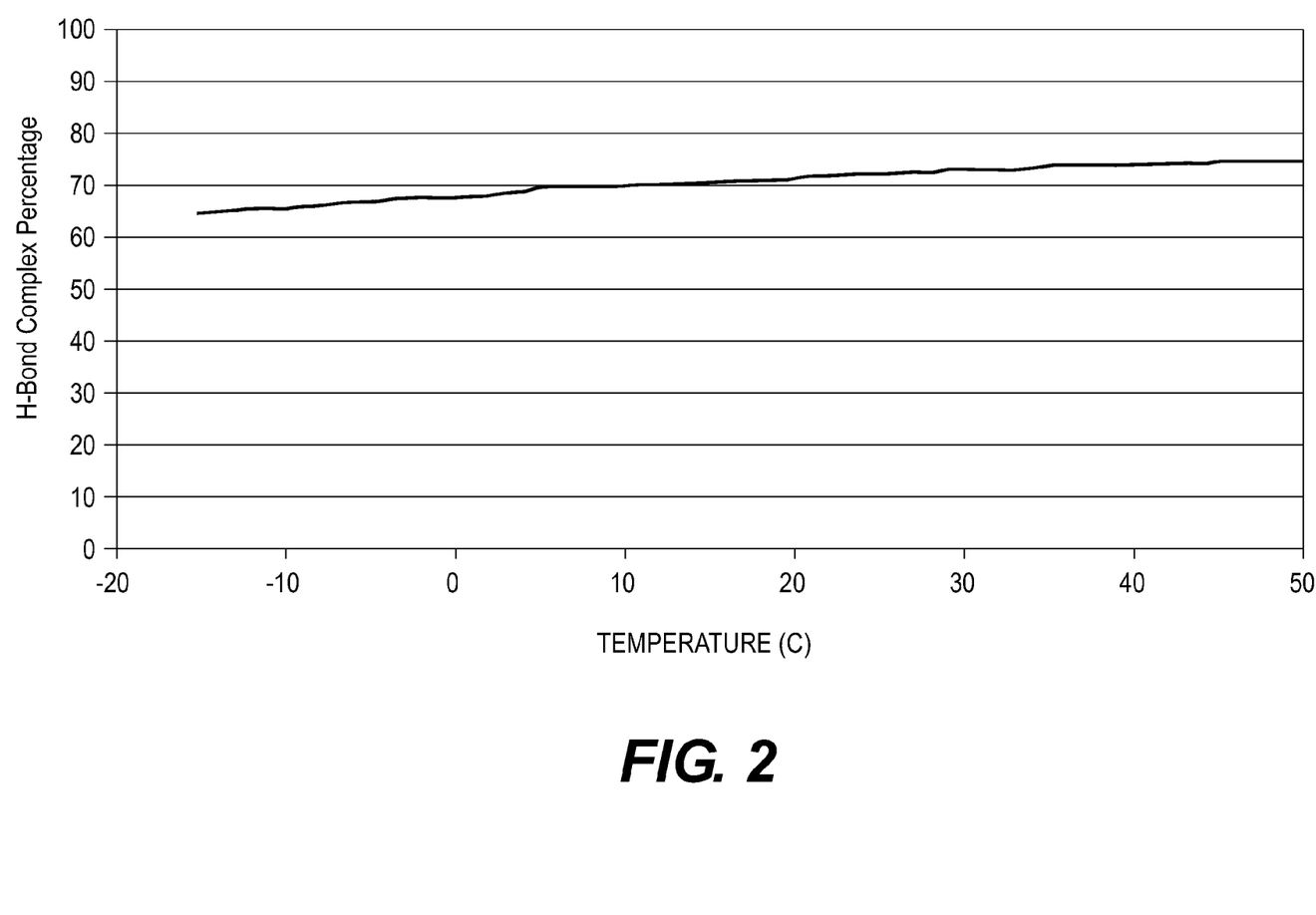
FIG. 2 is a plot of the percentage of HF molecules that are hydrogen bonded with water as function of temperature at 100% humidity, determined based on the equilibrium constant and water concentration at each temperature.

The competing temperature effects of a decreasing equilibrium constant and increasing maximum concentration of water available to form a hydrogen bond largely negate each other. As shown in FIG. 2, the opposing trends of decreasing equilibrium constant and increasing water partial pressure with temperature shown in FIG. 1 lead to a relatively shallow temperature dependence at 100% humidity. The plot is determined based upon the equilibrium constant and water concentration at each temperature as illustrated, for example, in FIG. 2. The fraction H-Bonded HF molecules is equal to:

$$\frac{[H_2O - HF]}{[H_2O - HF] + [HF]} = \frac{K_{eq}(T)[H_2O]}{K_{eq}(T)[H_2O] + 1} \qquad (Eq.\ 3)$$

Based upon Equation 2, the ratio of complexed to free HF species varies linearly with water concentration. In other words, there will be twice the amount of complexed HF molecules at 100% relative humidity when compared to 50% humidity conditions at the same temperature.

The saturation vapor pressure of water increases dramatically with increasing temperature. At higher temperatures there is much more water in the atmosphere to hydrogen bond with the HF, which drives the hydrogen bonding reaction to favor the complexed species. However, temperature plays a fairly mild role in determining the equilibrium populations because the two effects of a decreasing equilibrium constant, $K_{eq}(T)$, and an increasing availability of water with increasing temperature largely cancel each other. The product of the two effects can be seen in FIG. 2.

Relative humidity is the largest factor in determining the extent of hydrogen bond formation between HF and water in the atmosphere. Equation 2 can be rearranged into the following:

$$\frac{[H_2O - HF]}{[HF]} = K_{eq}(T)[H_2O]_{sat} \frac{[H_2O]}{[H_2O]_{sat}} \approx \alpha \cdot H_{rel}. \qquad (Eq.\ 4)$$

Figure 3:
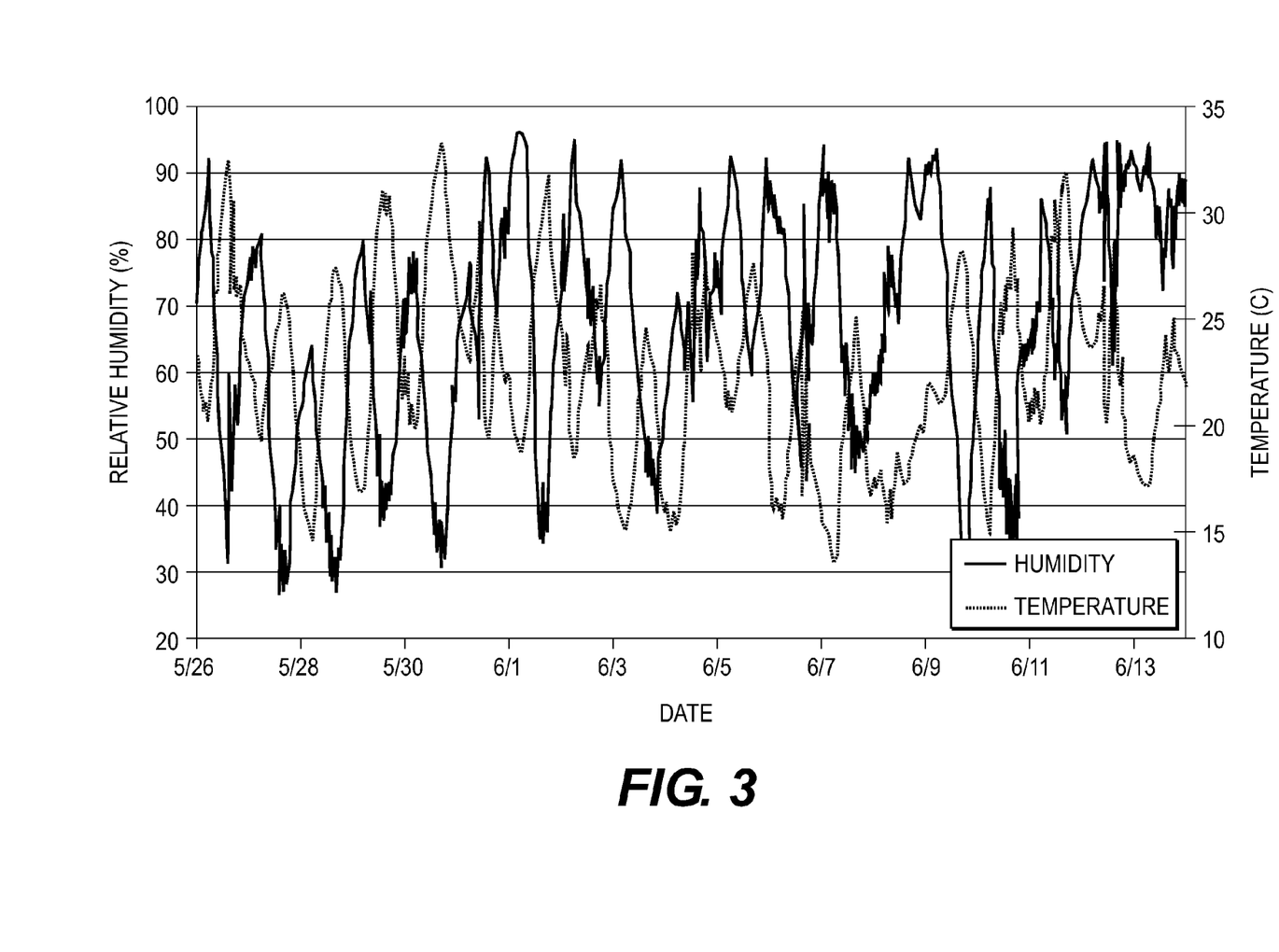
FIG. 3 is a plot of temperature and relative humidity over a 19 day period in a sample refinery where HF concentrations are measured.

FIG. 3 is a plot of $K_{eq}(T)[H_2O]_{sat}$, which varies little over a wide temperature range (15%), and can be roughly approximated by a constant term, $\alpha$. The term $[H_2O]/[H_2O]_{sat}$ represents relative humidity, $H_{rel}$. Relative humidity can vary in a short amount of time and influences the accuracy of the HF measurement.

FIG. 3 shows the temperature and humidity history in a mid-western refinery over a 19 day period. Relative humidity can change as much as 60% in several hours, which can grossly effect the accuracy of HF detection methods that only measure the free HF molecular species. Relative humidity is frequently inversely proportional to temperature, but relative humidity has a larger impact on the percentage of complexed HF molecules than temperature.

Figure 4:
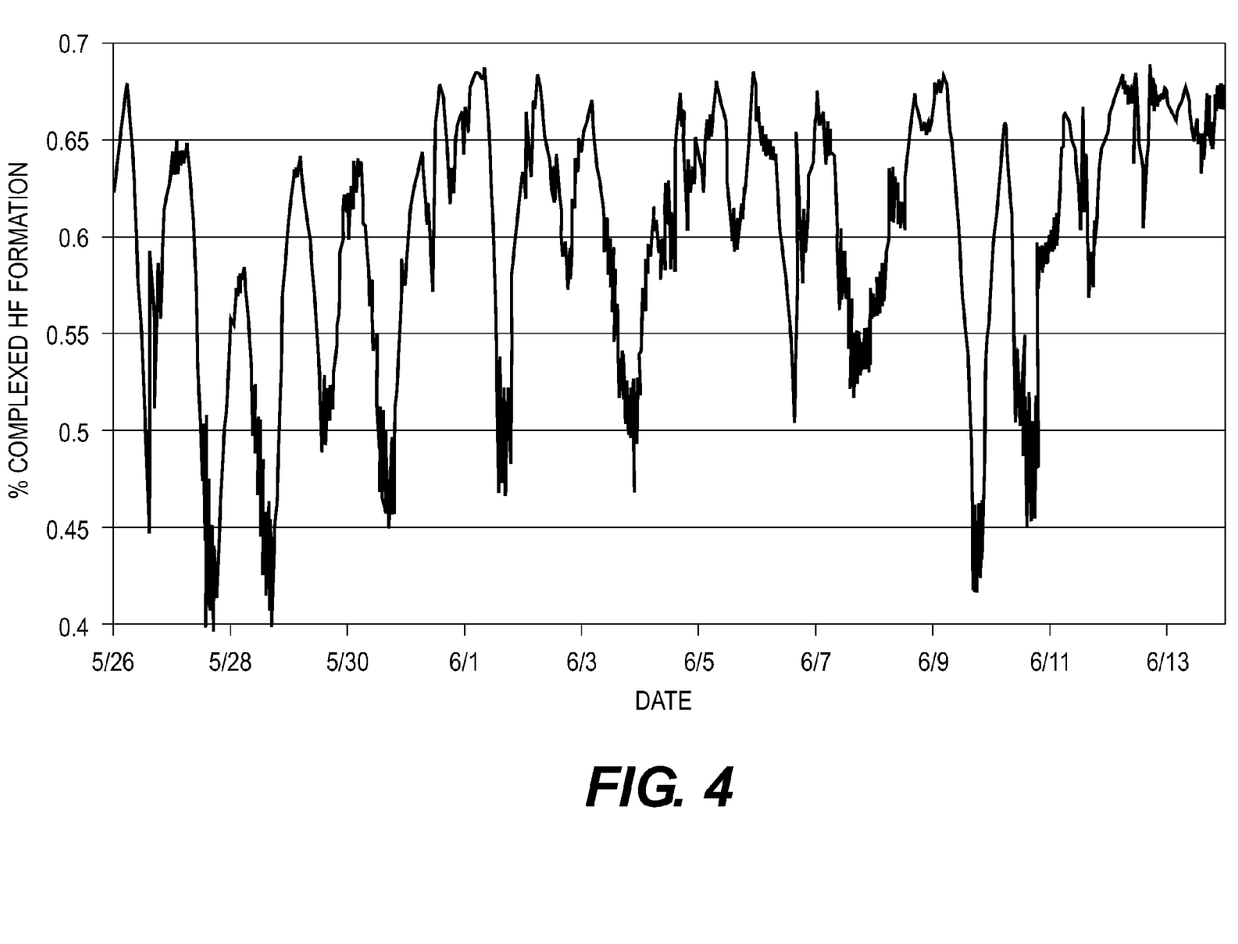
FIG. 4 is a plot of the percent of HF molecules that are expected to be complexed with water vapor based on the atmospheric conditions shown in FIG. 3.

Effects of the humidity and temperature changes on the percent of HF molecules that are complexed to water are shown in FIG. 4. It can be seen that over a period of several hours the population of complexed HF changes by approximately 25%. The plot was calculated using Equation 3. $[H_2O]_{sat}$ and $K_{eq}(T)$ were obtained from the data in FIG. 1. $[H_2O]$ was calculated based upon the following relationship:

$$[H_2O] = [H_2O]_{sat} \cdot H_{rel} \qquad (Eq.\ 5)$$

The relative humidity was converted to $[H_2O]$ based on the data shown in FIG. 1. Alternatively, the data from FIG. 2 can be stored as a look-up table. It is also contemplated that it can be determined as a function based upon either temperature and/or pressure.

When comparing the effect of water on the HF measurement between weather conditions at different sites, the potential error is more dramatic. HF alkylation plants can be located in dramatically different climates. For example, HF alkylation plants are located in Alberta, Canada and Louisiana, USA. Alberta can reach temperatures as low as −40° F. with low relative humidity (~30%), which would result in 15% of HF molecules bound to water. In contrast, temperatures in Louisiana can climb to 100° F. with relative humidity up to 90% resulting in 72% of HF bound to water. In the Louisiana case, detectors that only measure free HF may detect just slightly over a quarter of the total HF concentration.

Oligomerization of HF

Furthermore, HF is known to oligomerize with itself at high partial pressures and low temperatures. For the purposes of HF area monitoring, however, the concentrations of HF required for oligomer formation are so high as to saturate the detector from overwhelmingly high monomer signal before it interferes with quantification. Below 0.5 atm (500,000 ppm) virtually all HF exists as the free monomer species. Thus, around room temperature, HF partial pressures greater than 0.5 atm are required for oligomerization.

Further, oligomerization should not be a problem at low temperatures, as can be seen by the following example. As a first approximation, the dimer, $(HF)_2$, represents the predominant oligomer species.

$$HF + HF \xrightleftharpoons{K_{eq}} (HF)_2 \quad \text{(Eq. 6)}$$

The enthalpy for the reaction is 17.9 kJ/mol and the entropy is −94.6 J/mol·K. At −50° C. the equilibrium constant ($K_{eq}$) of the reaction is 0.176 atm$^{-1}$. see R. L Redington, *J. Phys. Chem.*, 86, 552 (1982), which is hereby incorporated by reference in their entirety.

Assuming a HF concentration of 10,000 ppm, which is many times greater than the lethal limit, the ratio of dimer to monomer concentration is expected to be:

$$\frac{[(HF)_2]}{[HF]} = K_{eq}(T)[HF] \quad \text{(Eq. 7)}$$
$$= (0.176 \text{ atm}^{-1}) \cdot (0.01 \text{ atm})$$
$$= 1.76 \times 10^{-3}$$

Therefore, for the purposes of area monitor detection, oligomerization can be disregarded even at very low temperatures.

Calibrating HF Detectors

Another aspect of the presently disclosed subject matter provides a method for calibrating an HF ambient air monitor including providing a carrier gas, introducing a constant, known flow of HF to the carrier gas to obtain a calibration sample, introducing the calibration sample to the HF ambient air monitor and measuring a first infrared absorption measurement at a wavelength corresponding to a vibrational frequency of an H—F bond within non-hydrogen bonded gas phase HF molecules, determining a carrier gas H$_2$O concentration metric in the calibration sample available for reaction with non-hydrogen bonded gas phase molecules present in the calibration sample at or about the time of obtaining the first infrared absorption measurement, calculating an uncorrected HF concentration metric in the calibration sample based on the constant, known flow of HF to the carrier gas, the carrier gas H$_2$O concentration metric and the reaction equilibrium relationship between uncomplexed HF and HF hydrate, and calibrating the HF ambient air monitor based on the first infrared absorption measurement and the uncorrected HF concentration metric in the calibration sample.

Calibration for tunable diode laser system sensors can be performed with a small porous-wall tube filled with HF that is kept at a constant temperature. A carrier gas flows around the tube and captures the HF that is permeating through the tube wall at a known rate. By adjusting the carrier gas flow, the desired concentration can be obtained for calibration. Even when the carrier gas used is ambient air, the humidity will vary (primary impact) and the temperature and flow rate for the carrier varies depending on the actual ambient conditions at which the test is done.

The ambient temperature and the humidity at the time of calibration can be measured, and the readings can be corrected to reflect the actual HF concentration based on thermodynamic functions that provide the partition between the HF monomer, polymers and hydrates. Currently, nitrogen gas is generally used as a carrier gas in tunable diode laser calibrations. Thus, the sensor is calibrated in the absence of HF hydrate and, once calibrated, the tunable diode laser will not account for the presence of the hydrate. Based on the presently disclosed subject matter, the laser can be calibrated using air as the carrier gas.

Correction Strategy for Water-HF Complex Formation

The extent of hydrogen bond formation between water and HF can be calculated and used to correct the unbound HF measurement giving the total HF concentration if the water concentration and temperature are known. Under the approximation that HF vapor exists only in the free and complexed-to-water states, the total HF concentration can be computed as $$P_{HFtotal} = P_{HF}(1 + K_P(T) P_{H_2O}) \quad \text{(Eq. 8)}$$

where $P_{HFtotal}$ is the total HF partial pressure, $P_{HF}$ is the detected (monomer) partial pressure, $P_{H2O}$ is the water partial pressure, and $K_P(T)$ is the temperature dependant equilibrium constant, which can be computed from the known thermodynamic quantities of the HF-water hydrogen bonding reaction.

The total HF concentration can be expressed as the sum of the free HF concentration and HF that has been complexed to water:

$$[HF]_{total}[HF] + [HF—H_2O] \quad \text{(Eq. 9)}$$

Using the relationship for the equilibrium constant describing the HF-water bond:

$$\frac{[H_2O - HF]}{[HF]} = K_{eq}(T)[H_2O] \quad \text{(Eq. 10)}$$

Combining the above two equations, total HF concentration can be expressed as:

$$[HF]_{total} = [HF] + [HF] K_{eq}[H_2O] \quad \text{(Eq. 11)}$$

Equation 11 can be rewritten as:

$$[HF]_{Total} = (1 + K_{eq}(T) \cdot [H_2O])[HF] \quad \text{(Eq. 12)}$$

Assigning a correction factor, and using Gibbs free energy to determine $K_{eq}(T)$, Equation 11 can be rewritten as:

$$[HF]_{Total} = C([H_2O], T)[HF] \quad \text{(Eq. 13)}$$

in which the correction factor, $C([H_2O], T)$, can be computed as:

$$C([H_2O], T) = 1 + [H_2O] e^{-\frac{\Delta G}{RT}} \quad \text{(Eq. 14)}$$

In which $\Delta G$ is the Gibbs free energy for the hydrogen bonding reaction between HF and water. In practice, $\Delta G$ is computed as:

$$\Delta G = \Delta H - T \Delta S \quad \text{(Eq. 15)}$$

The thermodynamic parameters for $\Delta H$ and $\Delta S$ are tabulated in literature. See, e.g., J. Chem. Soc. Faraday Trans., 1991, 87(3), 443-447), which is hereby incorporated by reference. The equations above can be used to make the HF concentration corrections in accordance with the presently disclosed subject matter.

Correction factors based on measurement conditions under three distinct temperatures and relative humidities are determined in the Examples.

There are several methods to simultaneously measure water concentration, temperature and uncorrected HF concentrations. Water concentration (typically expressed as partial pressure) is related to the relative humidity through the data shown in FIG. 1. Only ambient temperature is required to convert relative humidity to an absolute water concentration. Relative humidity measurements are typically inexpensive and can be installed on the HF area detector. The humidity measurement could be fed into the HF detector to make a correction using the detector's processor, or the humidity measurement could be reported to the DCS or external computer where the water correction could be performed.

Alternatively, sites already make meteorological measurements and measure relative humidity and ambient temperature. The water correction could then be made in a similar fashion as described in the above paragraph. In this embodiment, the water correction can be made external to the detector.

Additionally, water absorbs infrared radiation at nearby frequencies to most frequencies monitored to measure HF. Water can be simultaneously measured by the detector itself by analyzing the absorption spectrum and separating the water and HF components. In this case, the water correction is most practically made by the detector and it would output the corrected signal. In this circumstance, the detector itself would also be considered a hygrometer, even though a separate device that functions as a hygrometer in the traditional sense is not provided.

There are numerous ways one can make meteorological measurements required for the correction. Humidity, or $[H_2O]$, can be measured by a hygrometer. Most hygrometers measure relative humidity, which is related to $[H_2O]$ by:

$$R = [H_2O]/[H_2O]_{sat} \quad \text{(Eq. 16)}$$

The saturated water vapor concentration, $[H_2O]_{sat}$, at any given temperature, is well known and can be included in the algorithm. Dew point is a closely related measurement to humidity that can give $[H_2O]$. However, devices that measure dew point are typically also called dew point hygrometer, which is a type of a hygrometer.

Alternatively, the HF detector could measure water in the atmosphere directly. Water absorbs nearby in the infrared spectrum to HF. The HF detector could simultaneously measure HF and $H_2O$ and feed the $H_2O$ concentration into the HF correction factor. Water absorbs in many regions in the near-mid infrared spectrum. For example, the detector could either be equipped with two lasers to probe both the water and HF absorption bands, or the normal laser used to measure HF could be engineered also cover a water absorption region.

Alternatively, one can take the meteorological data from the site (manufacturing facilities often measure humidity and temperature) and make the correction in an external computer. The data can be downloaded from nearby weather stations.

Applications to Other Chemical Species

In addition to HF, several other toxic gas molecules (HCl, $H_2S$, and HCN) can hydrogen bond with water and consequently distort TDL spectroscopy measurements. While the effects would likely be several orders of magnitude less than for HF, the presently disclosed methods and systems can be applied to such other toxic gases. It is noted that HF is unique in that it forms an extremely strong hydrogen bond, as fluorine is the most electronegative element on the periodic table. Other notable toxic gas phase molecules will form much weaker hydrogen bonds, so hydrogen bond formation does not present as significant an issue as with HF.

EXAMPLES

The present invention is illustrated in greater detail by the specific examples presented below. It is understood that these examples are illustrative embodiments and are not intended to be limiting in any way.

Correction factors based on the presence of HF in hydrate form in three separate locations.

Location 1

Observed conditions: Temperature: 77° F., Relative Humidity: 60%.

The saturation vapor pressure of water at 77° F. is 23.6 Torr, as computed by the Goff-Gratch Equation for saturation vapor pressure over liquid water. See World Meteorological Organization (2000), General Meteorological Standards and Recommended Practices, Appendix A, WMO Technical Regulations, WMO-No. 49, corrigendum.

The absolute partial pressure of water at 60% relative humidity is 23.6 Torr×0.60=14.2 Torr. ΔG for the hydrogen bonding reaction is $\Delta G = \Delta H - T\Delta S$, and is thus:

=(−39.1 KJ/mol)−(298.15K)*(−0.0944 KJ/mol*K)=−10.9 KJ/mol $K_{eq}(T)$ for the hydrogen bonding reaction is:

$$K_{eq}(T) = \exp\left(-\frac{\Delta G}{RT}\right) = \exp\left(\frac{-10900 \frac{J}{mol}}{8.314 \frac{J}{mol \cdot K} \cdot 298.15K}\right) = 82.8$$

The ratio of hydrogen bonded HF molecules to free HF molecules can be expressed as:

$$\frac{[H_2O - HF]}{[HF]} = K_{eq}(T) \cdot [H_2O] = 82.8 \cdot \left(\frac{14.2}{760}\right) = 1.54$$

The fraction of hydrogen bonded HF molecules relative to the total HF population is:

$$\frac{[H_2O - HF]}{[HF] + [H_2O - HF]} = \frac{K_{eq}(T) \cdot [H_2O]}{K_{eq}(T) \cdot [H_2O] + 1} = \frac{1.54}{1.54 + 1} = 0.61$$

The correction factor, $C([H_2O],T)$ is computed as $C([H_2O],T) = K_{eq}(T).[H_2O]+1 = 1.54+1 = 2.54$ Location 2

Observed conditions: Temperature: 100° F., Relative Humidity: 90%.

The saturation vapor pressure of water at 100° F. is 49.7 Torr, as computed by the Goff-Gratch Equation for saturation vapor pressure over liquid water, set forth above. The absolute partial pressure of water at 90% relative humidity is 49.7 Torr×0.90=44.8 Torr.

ΔG for the hydrogen bonding reaction is $\Delta G = \Delta H - T\Delta S$ =(−39.1 KJ/mol)−(310.9K)*(−0.0944 KJ/mol*K)=−9.74 KJ/mol $K_{eq}(T)$ for the hydrogen bonding reaction is $$K_{eq}(T) = \exp\left(-\frac{\Delta G}{RT}\right) = \exp\left(\frac{-9740 \frac{J}{mol}}{8.314 \frac{J}{mol \cdot K} \cdot 310.9K}\right) = 43.3$$

The ratio of hydrogen bonded HF molecules to free HF molecules can be expressed as $$\frac{[H_2O-HF]}{[HF]} = K_{eq}(T) \cdot [H_2O] = 43.3 \cdot \left(\frac{44.8}{760}\right) = 2.55$$

The fraction of hydrogen bonded HF molecules relative to the total HF population is $$\frac{[H_2O-HF]}{[HF]+[H_2O-HF]} = \frac{K_{eq}(T) \cdot [H_2O]}{K_{eq}(T) \cdot [H_2O]+1} = \frac{2.55}{2.55+1} = 0.72$$

The correction factor, $C([H_2O],T)$ is computed as $$C([H_2O],T) = K_{eq}(T) \cdot [H_2O]+1 = 2.55+1 = 3.55$$

Location 3

Observed Conditions: Temperature: −40° F., Relative Humidity: 30%.

The saturation vapor pressure of water at −40° F. is 0.1 Torr, as computed by the Goff-Gratch Equation for saturation vapor pressure over ice. See World Meteorological Organization (2000), General Meteorological Standards and Recommended Practices, Appendix A, WMO Technical Regulations, WMO-No. 49, corrigendum.

The absolute partial pressure of water at 30% relative humidity is 0.1 Torr×0.30=0.03 Torr. ΔG for the hydrogen bonding reaction is ΔG=ΔH−TΔS=(−39.1 KJ/mol)−(233.15K)*(−0.0944 KJ/mol*K)=−17.1 KJ/mol.

$K_{eq}(T)$ for the hydrogen bonding reaction is:

$$K_{eq}(T) = \exp\left(-\frac{\Delta G}{RT}\right) = \exp\left(\frac{-17100 \frac{J}{mol}}{8.314 \frac{J}{mol \cdot K} \cdot 233.15K}\right) = 6731$$

The ratio of hydrogen bonded HF molecules to free HF molecules can be expressed as $$\frac{[H_2O-HF]}{[HF]} = K_{eq}(T) \cdot [H_2O] = 6731 \cdot \left(\frac{0.03}{760}\right) = 0.26$$

The fraction of hydrogen bonded HF molecules relative to the total HF population is $$\frac{[H_2O-HF]}{[HF]+[H_2O-HF]} = \frac{K_{eq}(T) \cdot [H_2O]}{K_{eq}(T) \cdot [H_2O]+1} = \frac{0.26}{0.26+1} = 0.21$$

The correction factor, $C([H_2O],T)$ is computed as $$C([H_2O],T) = K_{eq}(T) \cdot [H_2O]+1 = 0.26+1 = 1.26$$

The disclosed subject matter is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of determining a total HF concentration metric in an environment comprising:
    (a) measuring an uncorrected HF concentration metric in the environment based on a first infrared absorption measurement at a wavelength corresponding to a vibrational frequency of a non-hydrogen bonded gas phase HF molecule;
    (b) determining an ambient $H_2O$ concentration metric in the environment available for reaction with the non-hydrogen bonded gas phase HF molecules at or about the time of obtaining the first infrared absorption measurement;
    (c) calculating a HF hydrate concentration metric in the environment based on the uncorrected HF concentration metric, the ambient $H_2O$ concentration metric and a reaction equilibrium relationship between the non-hydrogen bonded gas phase HF molecule and the HF hydrate; and
    (d) determining the total HF concentration metric in the environment based on the uncorrected HF concentration metric and an amount of HF determined by the HF hydrate concentration metric.

2. The method of claim 1, wherein the infrared absorption measurement is obtained via an apparatus that employs a tunable diode laser.

3. The method of claim 1, wherein the ambient $H_2O$ concentration metric is determined based on the ambient temperature and a humidity metric selected from relative humidity and dew point, at or about the time of obtaining the first infrared absorption measurement.

4. The method of claim 1, wherein the ambient $H_2O$ concentration metric is determined by measuring a second infrared absorption measurement at a wavelength corresponding to a vibrational frequency of an H—O bond within $H_2O$ molecules at or about the time of obtaining the first infrared absorption measurement.

5. The method of claim 1, wherein the reaction equilibrium relationship between the gas phase HF molecule and the HF hydrate is based at least in part on the equilibrium constant, Keq(T), for the reaction $H_2O+HF \leftrightarrow HF.H_2O$ at the ambient temperature.

6. The method of claim 5, wherein the equilibrium constant, Keq(T), for the reaction $H_2O+HF \leftrightarrow HF.H_2O$ at the ambient temperature is calculated based at least in part on thermodynamic parameters for the hydrogen bonding reaction associated with the HF hydrate at the ambient temperature.

* * * * *